United States Patent
Yang et al.

(10) Patent No.: US 9,567,608 B2
(45) Date of Patent: Feb. 14, 2017

(54) METHODS OF NUCLEASE-BASED GENETIC ENGINEERING

(71) Applicants: Yi Yang, Belmont, MA (US); Marcello Maresca, Cambridge, MA (US)

(72) Inventors: Yi Yang, Belmont, MA (US); Marcello Maresca, Cambridge, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/632,497

(22) Filed: Feb. 26, 2015

(65) Prior Publication Data

US 2016/0032321 A1   Feb. 4, 2016

Related U.S. Application Data

(63) Continuation of application No. PCT/IB2013/058083, filed on Aug. 28, 2013.

(60) Provisional application No. 61/693,907, filed on Aug. 28, 2012.

(51) Int. Cl.
*C12N 15/90* (2006.01)
*C12N 15/10* (2006.01)
*C12N 15/85* (2006.01)

(52) U.S. Cl.
CPC ............ *C12N 15/90* (2013.01); *C12N 15/102* (2013.01); *C12N 15/85* (2013.01); *A01K 2217/00* (2013.01); *C12N 2800/80* (2013.01)

(58) Field of Classification Search
CPC .... C12N 15/90; C12N 15/907; C12N 2800/80
See application file for complete search history.

(56) References Cited

U.S. PATENT DOCUMENTS

2013/0326645 A1* 12/2013 Cost ................. C12N 15/85
800/14

FOREIGN PATENT DOCUMENTS

WO       2011100058 A1   8/2011

OTHER PUBLICATIONS

Kuhlman et al. Site-specific chromosomal integration of large synthetic constructs. Nucleic Acids Research, vol. 38, No. 6, e92, Jan. 4, 2010, printed as pp. 1/10-10/10.*
Cristea et al., In vivo cleavage of transgene donors promotes nuclease-mediated targeted integration. Biotechnol Bioeng. Mar. 2013;110(3):871-80.
Cui et al., Targeted integration in rat and mouse embryos with zinc-finger nucleases. Nat Biotechnol. Jan. 2011;29(1):64-T.
Maresca et al., Obligate ligation-gated recombination (ObLiGaRe): custom-designed nuclease-mediated targeted integration through nonhomologous end joining. Genome Res. Mar. 2013;23(3):539-46.
Meyer et al., Gene targeting by homologous recombination in mouse zygotes mediated by zinc-finger nucleases. Proc Natl Acad Sci U S A. Aug. 24, 2010;107(34):15022-6.
Orlando et al., Zinc-finger nuclease-driven targeted integration into mammalian genomes using donors with limited chromosomal homology. Nucleic Acids Res. Aug. 2010;38(15):e152 (15 pages).

* cited by examiner

*Primary Examiner* — Jennifer Dunston

(57) ABSTRACT

The present invention relates to genetic techniques employing the direct ligatation of an external DNA fragment generated in situ by the same ZFNs that target the genome. ObLiGaRe, i.e., the obligated ligation-gated recombination, is a new method for genetic engineering using custom designed nucleases, and a strategy of site-specific gene insertion utilizing the NHEJ pathway. It applies a similar logic to the one used in unidirectional loxP sites (Oberdoerffer et al., 2003) but maintains all the advantages and flexibility of CDNs.

1 Claim, 15 Drawing Sheets

5' junction

```
1 acccacagtggggccCAacccactgtggggt  SEQ ID NO: 29
2 acccacagtggggccacccactgtggggt    SEQ ID NO: 27
3 acccacagtggggccacccactgtggggt    SEQ ID NO: 27
4 acccacagtggggccacccactgtggggt    SEQ ID NO: 27
```

3' junction

```
atcctgtccctagggacactagggacaggat  SEQ ID NO: 30
atcctgtccctagggacactagggacaggat  SEQ ID NO: 30
atcctgtccctagggacactagggacaggat  SEQ ID NO: 30
atcctgtccctagggacactagggacaggat  SEQ ID NO: 30
```

5' junction

```
1 acccacagtggggccacccactgtggggt    SEQ ID NO: 27
2 acccacagtggggccacccactgtggggt    SEQ ID NO: 27
3 acccacagtggggccacccactgtggggt    SEQ ID NO: 27
4 acccacagtggggccacccactgtggggt    SEQ ID NO: 27
```

3' junction

```
atcctgtccctagggacactagggacaggat  SEQ ID NO: 30
atcctgtccctagggacactagggacaggat  SEQ ID NO: 30
atcctgtccctagggacactagggacaggat  SEQ ID NO: 30
atcctgtccctagggacactagggacaggat  SEQ ID NO: 30
```

5' junction

```
1 acccacagtgg----------ggt         SEQ ID NO: 31
2 acccacagtggggccacccactgtggggt    SEQ ID NO: 27
3 acccacagtgg----------ggt         SEQ ID NO: 31
4 acccacagtggggccacccactgtggggt    SEQ ID NO: 27
```

3' junction

```
atcctgtcc----------ctagggacaggat  SEQ ID NO: 32
atcctgtgt-------ccactagggacaggat  SEQ ID NO: 33
atcctgtcc----------ctagggacaggat  SEQ ID NO: 32
del 66 bp
atcctgtccctagggacactagggacaggat   SEQ ID NO: 28
atcctgtccctagg----------acaggat   SEQ ID NO: 34
```

Continued from FIG.1B-1

FIG.1B-2

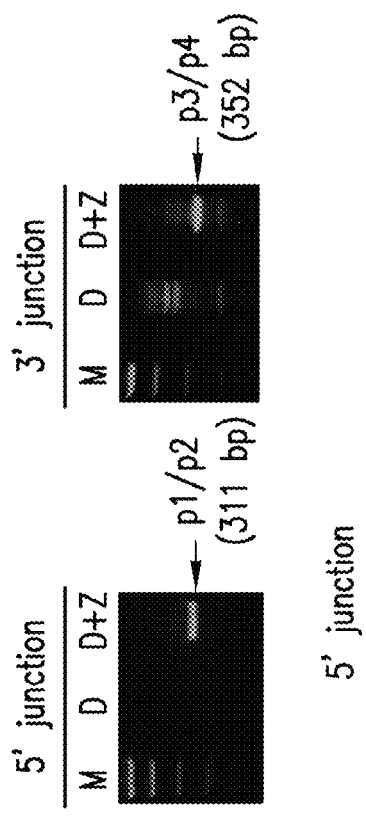

5' junction
1 acctgcctgctgg------acagcaggggcaggt SEQ ID NO: 44
2 acctgcctgctggacatacagcaggcaggt SEQ ID NO: 42
3 acctgcctgctggACacatacagcaggcaggt SEQ ID NO: 47
4 acctgcctgctggacatacagcaggcaggt SEQ ID NO: 42
5 acctgcctgctggacatacagcaggcaggt SEQ ID NO: 42
6 acctgcctgctggacatacagcaggcaggt SEQ ID NO: 42

3' junction
ttgtccagctgtgtccaggacatactggacacagctggacaag SEQ ID NO: 45
ttg------actggacacagctggacaag SEQ ID NO: 46
ttgtccagctgtgtccaggacatactggacacagctggacaag SEQ ID NO: 45
ttgtccagctgtgtccaggacatactggacacagctggacaag SEQ ID NO: 45
ttgtccagctgtgtccaggacatactggacacagctggacaag SEQ ID NO: 45
ttgtccagctgtgtccaggacatactggacacagctggacaag SEQ ID NO: 45

FIG.3C

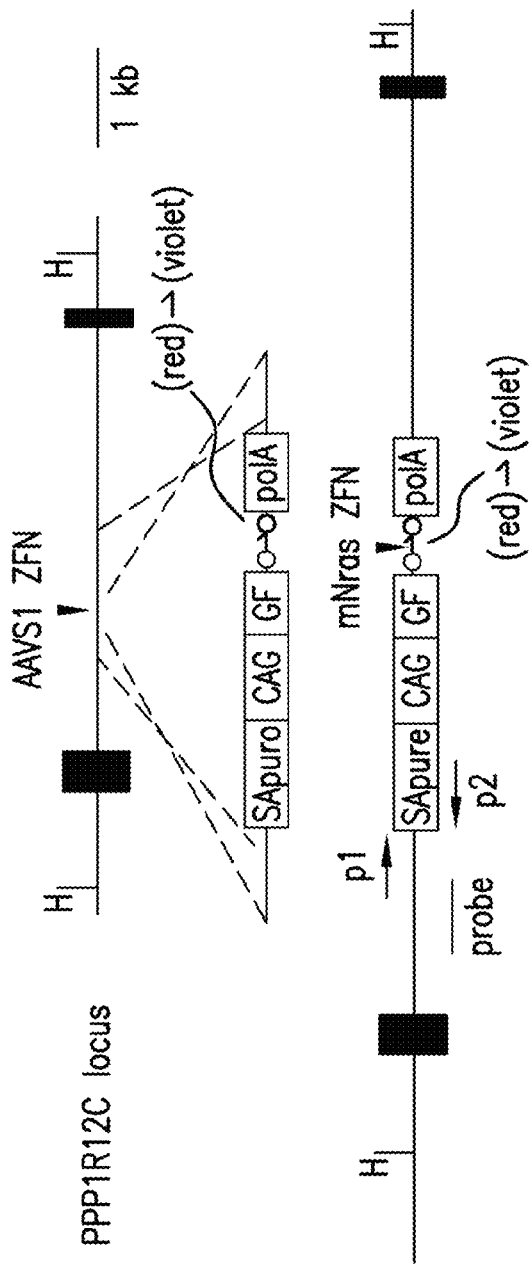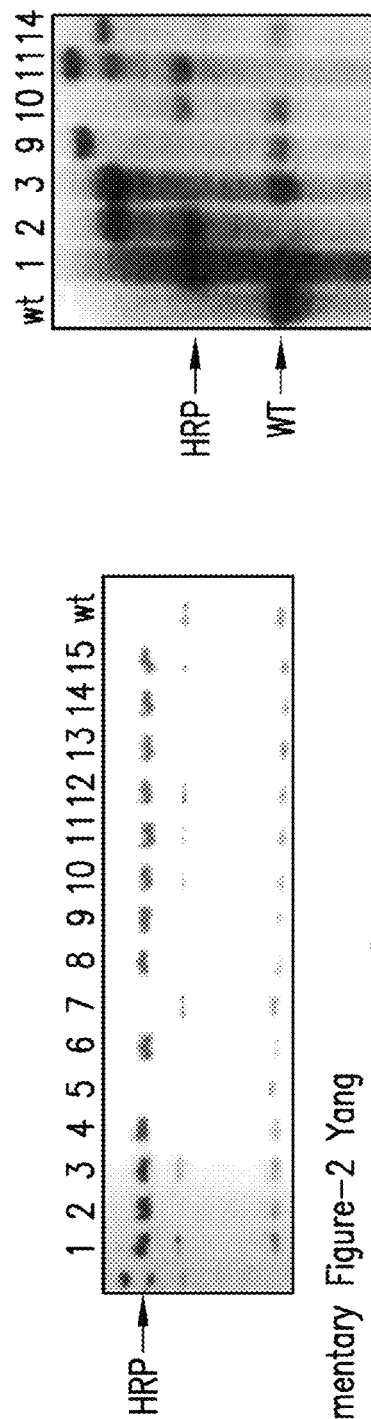
FIG. 7A
FIG. 7B
FIG. 7C

METHODS OF NUCLEASE-BASED GENETIC ENGINEERING

SEQUENCE LISTING

The instant application contains a Sequence Listing which has been submitted electronically in ASCII format and is hereby incorporated by reference in its entirety. Said ASCII copy, created on Jun. 10, 2016, is named PAT055232-US-CNT_SL.txt and is 13,903 bytes in size.

BACKGROUND OF THE INVENTION

The development of CDNs including ZFNs and TALENs has made it possible to perform precise genetic engineering in many cell types and species (Bibikova et al., 2003; Christian et al., 2010; Hockemeyer et al., 2009; Kim et al., 1996; Meyer et al., 2010; Moehle et al., 2007; Porteus and Baltimore, 2003; Urnov et al., 2010). These are hybrid endonucleases consist of a FokI nuclease domain and a DNA binding domain assembled from optimized DNA binding modules that are specific for either single nucleotide (for TALENs) or trinucleotide motifs (for ZFNs). Once introduced in cells, these enzymes generate a DSB in the genome at or near the desired modification site. This event induces the natural DDR process to mend the breakage (Rouet et al., 1994). The primary pathway is NHEJ in which the two ends are processed and ligated together with nucleotide insertions and deletions. Though highly efficient, this mechanism can only produce functional knockout alleles that are often heterogeneous and difficult to isolate without clonal selection. Accurate gene modification relies on HR in which exogenous DNA fragments flanked by homology sequences around the DSB site can be copied faithfully from a template with defined boundaries (Rouet et al., 1994).

Targeted gene modification has been almost exclusively mediated by homologous recombination. Though CDNs have made gene targeting feasible in cell lines that have low intrinsic HR efficiency, NHEJ is still the dominant DSB repair pathway. As a result, KO alleles generated by NHEJ are obtained at a much higher frequency than KI alleles generated by HR. A deficiency in NHEJ can significantly promote HR as seen in *E. coli* in which NHEJ is neglectable (Liang et al., 1996; Maresca et al., 2010).

SUMMARY OF THE INVENTION

We have successfully applied ZFNs on generating knock-out or knock-in alleles directly in mouse zygotes as reported in the literature (Cui et al., 2011; Meyer et al., 2010). While optimizing gene targeting conditions, we observed that a donor plasmid can be "ligated" into the genome if it contained the same ZFN recognition sites. It had been reported that short double strand DNAs with 5' overhangs could be ligated to the complementary ends generated after ZFN digestion (Orlando et al., 2010). This observation has not been further explored probably because it requires the knowledge of the overhangs generated by ZFNs and its application is limited to small oligonucleotide insertions (Orlando et al., 2010). Furthermore, it had also been shown that sometimes donor molecules including single strand oligodeoxynucleotides (ssODNs) (Chen et al., 2011; Radecke et al., 2010) and larger external linear sequences could be captured at DSB sites generated by ZFNs (Fung and Weinstock, 2011; Li et al., 2011; Mittelman et al., 2009). This feature has been harnessed to track "off-target" effects of the homing endonuclease I-SceI and ZFNs (Petek et al., 2010). Based on these reports and our own observation in mouse embryos, we surmised that it should be possible to directly ligate an external DNA fragment generated in situ by the same ZFNs that target the genome.

We took advantage of the obligated herterodimeric property of the CDNs (Doyon et al., 2011; Miller et al., 2007; Ramalingam et al., 2011; Szczepek et al., 2007) and designed a strategy to achieve efficient and precise gene targeting without homology in the donor plasmid. We named this method ObLiGaRe (Obligated Ligation-Gated Recombination) to reflect the etymologic meaning of the Latin verb obligare (to ligate head to head). It is broadly applicable in different cell lines and provides an additional approach for genetic engineering.

In this study we developed ObLiGaRe, a strategy of site-specific gene insertion utilizing the NHEJ pathway. It applies a similar logic to the one used in unidirectional loxP sites (Oberdoerffer et al., 2003) but maintains all the advantages and flexibility of CDNs. The alternate design of the ZFNs site that we insert in the vector is necessary and sufficient to achieve precise end joining of the vector in the genomic ZFN site. Though less frequent, we did observe that aberrant joining products involving small deletions or insertions at the junctions. We speculated that these might result from processing alternative overhang types generated by the same ZFNs that were mismatched (Hockemeyer et al., 2009; Orlando et al., 2010; Smith et al., 2000; Zeevi et al., 2008). We never observed precise insertion of the vector at targeted genomic locus when a ZFNs site identical to the one present in the genome is introduced in the vector. In fact no integration of a surrogate reporter plasmid bringing a ZFNs site identical to the one in the genome was observed in a recent study (Kim et al., 2011). ObLiGaRe eliminates cloning homology arms into the donor vector and does not require any previous knowledge of the overhangs generated by specific CDNs.

ObLiGaRe is applicable with both ZFNs and TALENs (FIG. 6A-6B) and can be used as a high throughput method for screening potent CDNs replacing the current Cel-I assay (Reyon et al., 2012) It works in a wide variety of cell types including KBM7 and C2C12 cells in which precise gene insertion has not be demonstrated. We are currently testing whether it can be used in primary, non replicating cells in which NHEJ seems to be the predominant pathway to repair DSBs. We are also exploring whether it can work in embryos of mice and zebrafish. Finally we inserted the largest construct in the genome by ZFN to date (FIG. 3) and we predict that we can use it to deliver even larger construct such as BACs into a pre-defined genomic locus, which is very challenging, if not impossible, to achieve via HR.

Beyond the practical value of our method, it can be used as a new tool in the study of NHEJ and the crosstalk between NHEJ and HR. Although similar strategies were reported using the I-SceI homing endonuclease (Certo et al., 2011), our strategy allows us to track any endogenous locus that can be targeted by ZFNs. We are interested in using this reporter system to monitor differential utilizations of NHEJ and HR in cells before and after oncogenic transformation. We are also continuing to identify chemical and genetic modulators that influence the cells to choose NHEJ or HR.

BRIEF DESCRIPTION OF THE DRAWINGS

FIGS. 1A-1B ObLiGaRe at AAVS1 locus.
FIG. 1A Schematic illustration of ObLiGaRe strategy. ZFN recognition sites are indicated as grey and blue circles with the corresponding sequences displayed. The predicted joining sequences between the vector and the genome are shown. The insertion of the vector in the AAVS1 locus will cause a size shift from 6.7 kb (WT) to 14.2 kb (LP) of a HindIII (H) digested fragment. AAVS1 internal probe (int) and vector specific probe (CM) are indicated in the map at the hybridization sites. Figure discloses SEQ ID NOS 25-28, respectively, in order of appearance.

FIG. 1B-1 shows Southern blot of 4 puro resistant colonies after ObLiGaRe at AAVS1 locus in HCT116 (upper), RKO (middle) and KBM-7 (lower) with int probe (left) and CM probe (right). FIG. 1B-2 shows the sequences at the 5' and 3' junctions corresponding to each clones from FIG. 1B-1, with the upper sequences (SEQ ID NOS 29-30, 27, 30, 27, 30, 27 and 30, respectively, in order of appearance) from HCT116, the middle sequences (SEQ ID NOS 27, 30, 27, 30, 27, 30, 27 and 30, respectively, in order of appearance) from RKO, and the lower sequences (SEQ ID NOS 31-33, 27, 32, 31, 27-28 and 34, respectively, in order of appearance) from KBM-7. Insertions are indicated as capital letters, deletions are indicated as dotted lines.

FIG. 2A Strategy for targeting human PTEN (left) and PTENP1. PTEN ZFN recognition sites are indicated as orange and cyan circles with the corresponding sequences displayed. The predicted joining sequences between the vector and the genome are indicated. The insertion of the vector will cause a size shift of a BsrGI (B) digested fragment from wild type of 2.4 kb (WT) to the ligation product of 7.8 kb (LP) at PTEN locus and 25.6 kb (WT) to 31.0 kb (LP) at PTENP1 locus. AAVS1 internal probe (int) and vector specific probe (CM) are indicated in the map at the hybridization sites. Figure discloses SEQ ID NOS 35-36, 38 and 37, respectively, in order of appearance.

FIG. 2B Southern blots using probes specific for PTEN (PT, left), PTENP1 (P1 middle), and the vector (CM, right) for 4 G418 resistant colonies. The sequence of the 5' junction between PTEN or PTENP1 and mCherry are indicated in the table. Insertions are indicated in capital letters and "ins," where "ins" represents a 224 bp insertion. Figure discloses SEQ ID NOS 38, 38, 38, 57, 39, 38 and 38, respectively, in order of appearance.

FIGS. 3A-3C ObLiGaRe in C2C112 and MEF cells.

FIG. 3A Strategy for targeting Nras locus in MEF and C2C12 cells. Nras ZFN sites are indicated as violet and red circles with the corresponding sequences displayed. The predicted joining sequences between the vector and the genome are shown. Primers for PCR detection of the junctions and probes (CM and NR) are indicated. The insertion of the vector will cause a size shift of an NdeI (N) digested fragment from wild type of 6.2 kb (WT) to the ligation product of 11.6 kb (LP) at Nras locus. AAVS1 internal probe (int) and vector specific probe (CM) are indicated in the map at the hybridization sites. Figure discloses SEQ ID NOS 40-43, respectively, in order of appearance.

FIG. 3B Southern blot for 4 C2C12 clones expressing mCherry. LP indicates the expected ligation product band upon integration of the vector in the genome.

FIG. 3C Genomic PCR products amplified from pools of MEFs after transfection with ObLiGaRe donor alone (V) or co-transfection with ObLiGaRe donor and Nras ZFNs (V+I). P1-P2 primers amplify the 5' junction and P3-P4 primes amplify the 3'junction. The table lists the sequences of 5' and 3' junctions from pooled MEF cells obtained by cloning the genomic PCR products into TOPO TA vectors followed by sequences. Deletions are indicated as dotted lines and insertion in capital letters. Figure discloses SEQ ID NOS 44-45, 42, 46-47, 45, 42, 45, 42, 45, 42 and 45, respectively, in order of appearance.

FIG. 4A Strategy to introduce an inducible gene expression cassette. ZFN cutting sites are the same as in FIG. 1. The expression of rtTA is controlled by the constitutive CAG promoter while GFP is under the doxycycline responsive promoter (tetO). The STOP sign indicates a transcription termination cassette. Int and CM represent the probe for Southern blot. P1-P2 and P3-P4 are PCR primers used to amplify the 5' and 3' junctions. K: KpnI.

FIG. 4B Southern blot of 8 positive clones is showed with both internal (int) and vector specific probe (CM). LP product indicates the expected ligation product upon vector integration. The sequence for 5' and 3' junction of the 8 clones are reported in the table on the right with dotted lines indicate deletions. Figure discloses SEQ ID NOS 48, 28, 27, 49, 27-28, 27-28, 27-28, 27-28, 27-28, 50 and 28, respectively, in order of appearance.

FIG. 4C GFP fluorescence is detected by fluorescence microscopy in cells from Clone No. 6 without (−) and with (+) 48 hr treatment of 1 μg/ml doxycycline (dox).

FIG. 5A Illustration of the reporter DGF cassette in the AAVS1 locus. ZFN sites are the same as in FIG. 3. A functional GFP is generated after HR using the HA plasmid as donor, while a functional mCherry is inserted upon ObLiGaRe using the ObLiGaRe donor. The two donors are about the same size.

FIG. 5B Determination of fluorescent cells number after co-transfection of Nras ZFN, ObLiGaRe and HA donors by FACS. Detection of GFP and mCherry cells were gated using parental cells (WT, left) which did not show any fluorescent cells upon co-transfection. When the reporter cell line was contrafected with the 3 constructs, GFP and mCherry cells were shown in their corresponding gates (DGF, right).

FIG. 5C Representation of the percentage of GFP and mCherry positive cells out of total live cells in WT HCT116 cells, reporter HCT116 cells, without any treatment (DGF) or after treatment with 10 M Nu7026 or 4 mM Caffeine. Error bars: standard deviation; n=3.

FIG. 6A Schematic illustration of ObLiGaRe strategy at PPP1R12C (AAVS1) locus with TALENs. TALENs recognition sites are indicated as grey and blue circles connected with small arrows (cutting sites). The DNA sequence of AAVS1 specific TALENs site (wt) and the ObLiGaRe TALENs site (iv) are shown. The predicted joining sequences after precise end joining between the vector and the genome are indicated. Figure discloses SEQ ID NOS 51-54, respectively, in order of appearance.

FIG. 6B Southern blot of 6 puromycin resistant clones after ObLiGaRe. LP indicates the predicted ligation product. The probes are the same as used in FIG. 1. The 5' and 3' junction sequences of the 6 clones are in the tables on the right. S: SphI. Figure discloses SEQ ID NOS 53, 53, 53, 55, 53, 56, 53-54, 54, 54, 54 and 54, respectively, in order of appearance.

FIG. 6B Southern blot of 6 puromycin resistant clones after ObLiGaRe. LP indicates the predicted ligation product. The probes are the same as used in FIG. 1. The 5' and 3' junction sequences of the 6 clones are in the tables on the right. S: SphI.

FIGS. 7A-7C Generate a reporter cell line for monitoring HR vs. ObLiGaRe.

FIG. 7A Strategy of inserting the DGF reporter at the AAVS1 locus. Primers used for PCR screening (P1-P2) and probe for Southern blot (int) are reported in the map.

FIG. 7B Genomic PCR screening of 15 puromycin resistant colonies for the insertion of the puro cassette at PPP1R12C locus.

FIG. 7C Southern blot of the seven clones identified after PCR screening. WT indicates the expected wild type band upon HindIII (H) digestion. HRP indicates the expected homologous recombination product upon correct integration at PPP1R12C locus. Clone#10 was used for the experiments described in FIG. 5.

DETAILED DESCRIPTION OF THE INVENTION

Figure 1A:
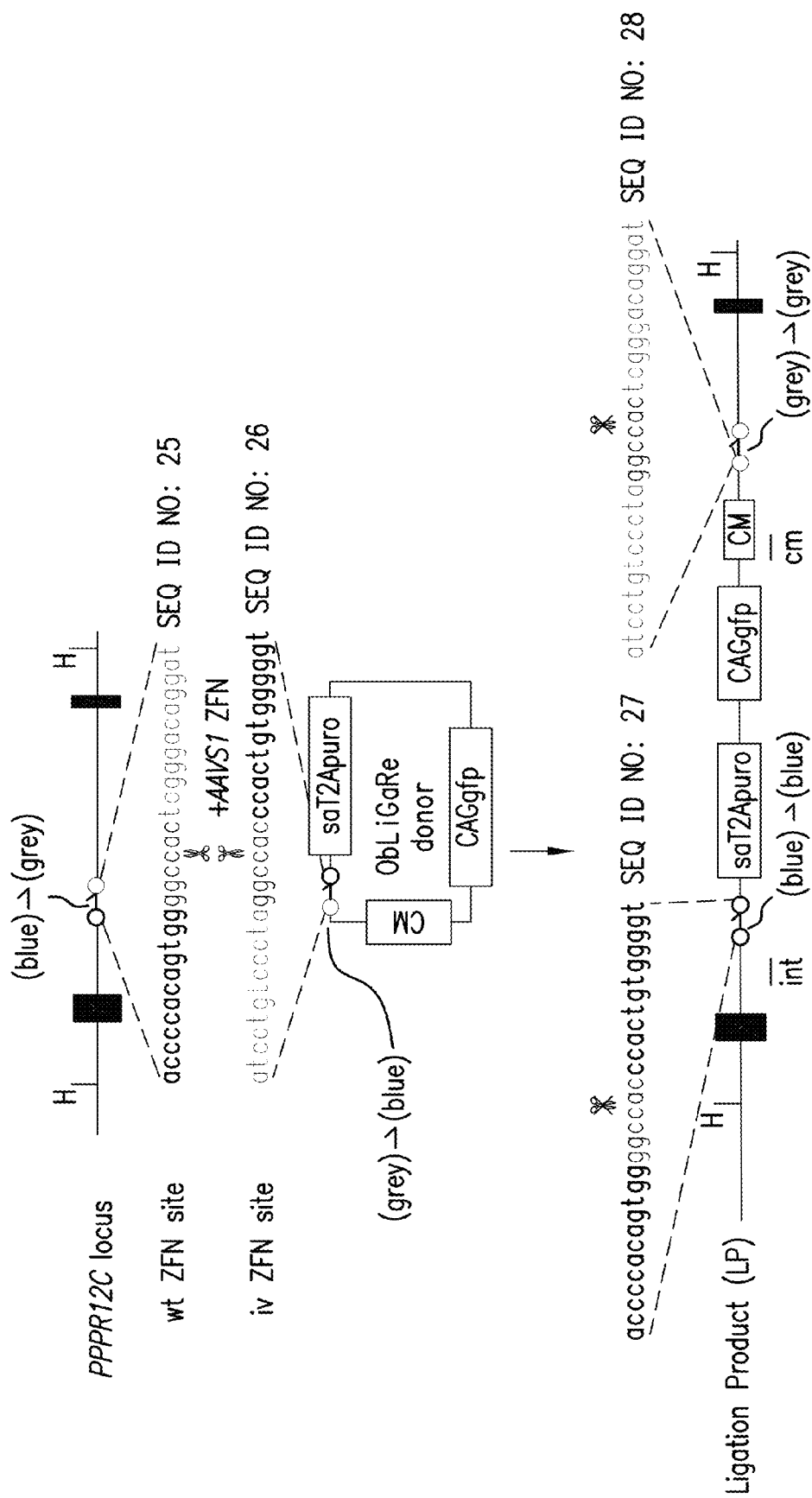

We have successfully applied ZFNs on generating knock-out or knock-in alleles directly in mouse zygotes as reported in the literature (Cui et al., 2011; Meyer et al., 2010). While optimizing gene targeting conditions, we observed that a donor plasmid can be "ligated" into the genome if it contained the same ZFN recognition sites. It had been reported that short double strand DNAs with 5' overhangs could be ligated to the complementary ends generated after ZFN digestion (Orlando et al., 2010). This observation has not been further explored probably because it requires the knowledge of the overhangs generated by ZFNs and its application is limited to small oligonucleotide insertions (Orlando et al., 2010). Furthermore, it had also been shown that sometimes donor molecules including single strand oligodeoxynucleotides (ssODNs) (Chen et al., 2011; Radecke et al., 2010) and larger external linear sequences could be captured at DSB sites generated by ZFNs (Fung and Weinstock, 2011; Li et al., 2011; Mittelman et al., 2009). This feature has been harnessed to track "off-target" effects of the homing endonuclease I-SceI and ZFNs (Petek et al., 2010). Based on these reports and our own observation in mouse embryos, we surmised that it should be possible to directly ligate an external DNA fragment generated in situ by the same ZFNs that target the genome.

We took advantage of the obligated herterodimeric property of the CDNs (Doyon et al., 2011; Miller et al., 2007; Ramalingam et al., 2011; Szczepek et al., 2007) and designed a strategy to achieve efficient and precise gene targeting without homology in the donor plasmid. We named this method ObLiGaRe (Obligated Ligation-Gated Recombination) to reflect the etymologic meaning of the Latin verb obligare (to ligate head to head). It is broadly applicable in different cell lines and provides an additional approach for genetic engineering.

In this study we developed ObLiGaRe, a strategy of site-specific gene insertion utilizing the NHEJ pathway. It applies a similar logic to the one used in unidirectional loxP sites (Oberdoerffer et al., 2003) but maintains all the advantages and flexibility of CDNs. The alternate design of the ZFNs site that we insert in the vector is necessary and sufficient to achieve precise end joining of the vector in the genomic ZFN site. Though less frequent, we did observe that aberrant joining products involving small deletions or insertions at the junctions. We speculated that these might result from processing alternative overhang types generated by the same ZFNs that were mismatched (Hockemeyer et al., 2009; Orlando et al., 2010; Smith et al., 2000; Zeevi et al., 2008). We never observed precise insertion of the vector at targeted genomic locus when a ZFNs site identical to the one present in the genome is introduced in the vector. In fact no integration of a surrogate reporter plasmid bringing a ZFNs site identical to the one in the genome was observed in a recent study (Kim et al., 2011). ObLiGaRe eliminates cloning homology arms into the donor vector and does not require any previous knowledge of the overhangs generated by specific CDNs.

Figure 6A:
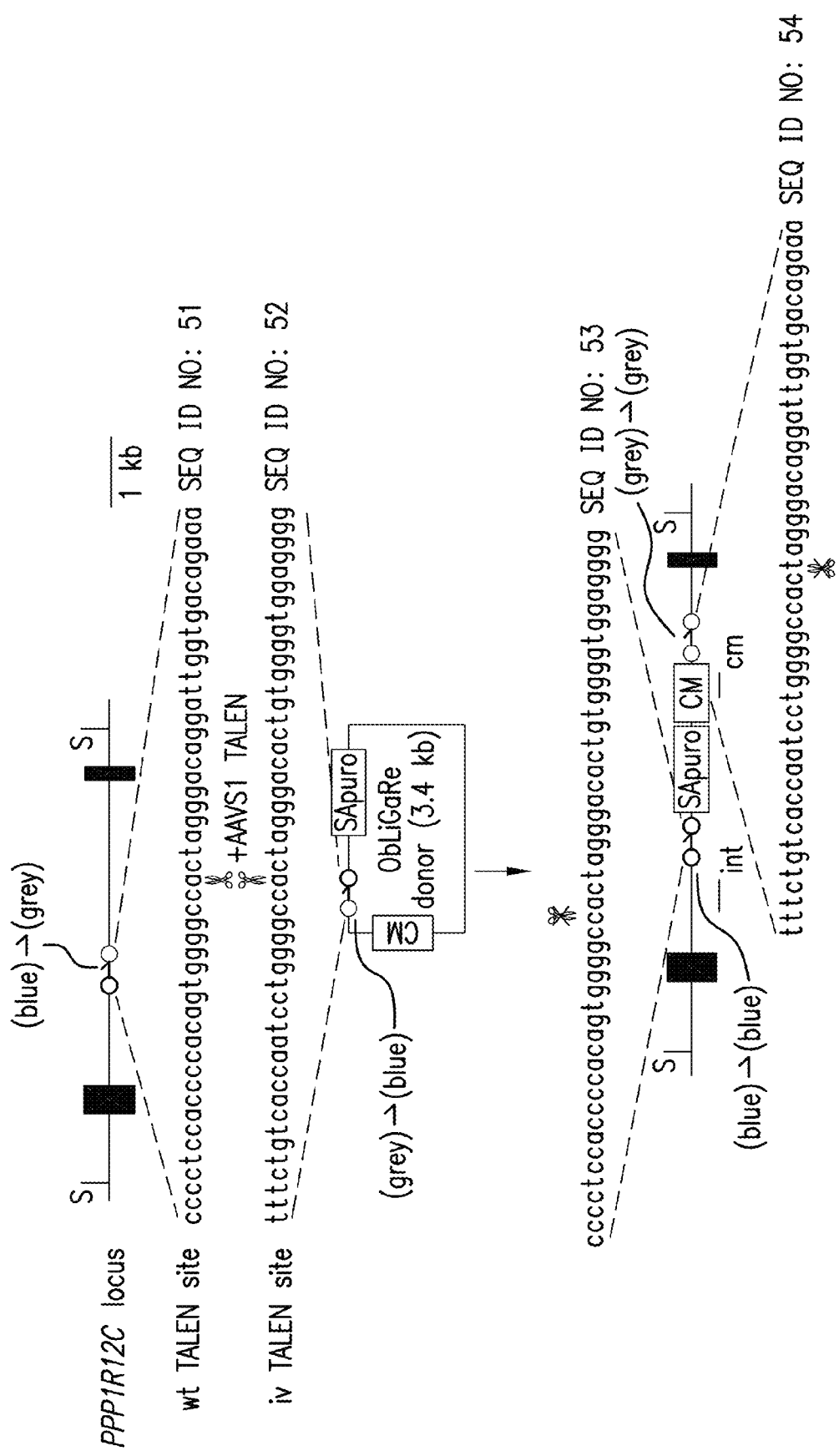
FIGS. 6A-6B ObLiGaRe using AAVS1 TALEN.
Figure 6B:
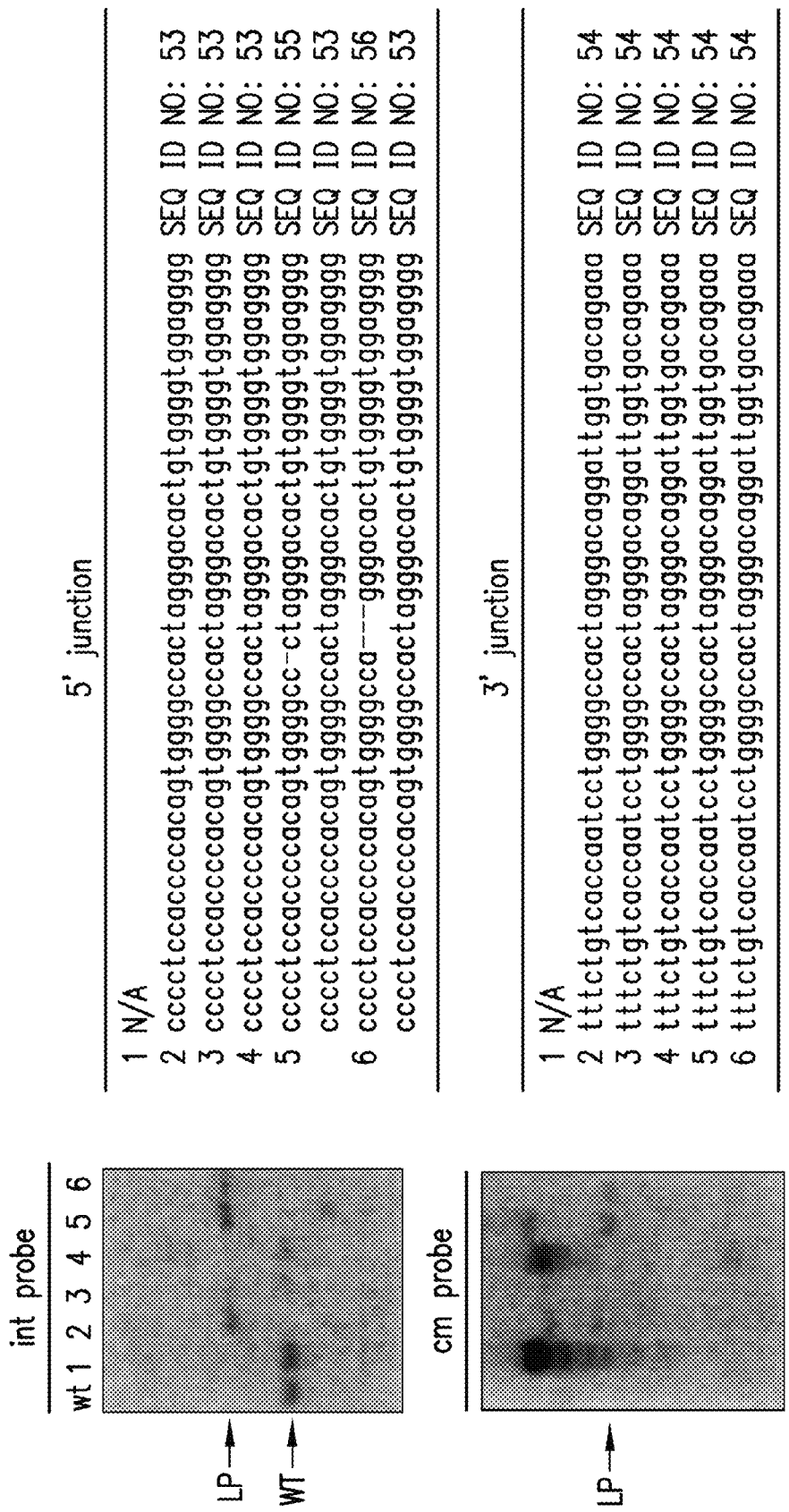

ObLiGaRe is applicable with both ZFNs and TALENs (FIG. 6A-6B) and can be used as a high throughput method for screening potent CDNs replacing the current Cel-I assay (Reyon et al., 2012) It works in a wide variety of cell types including KBM7 and C2C12 cells in which precise gene insertion has not be demonstrated. We are currently testing whether it can be used in primary, non replicating cells in which NHEJ seems to be the predominant pathway to repair DSBs. We are also exploring whether it can work in embryos of mice and zebrafish. Finally we inserted the largest construct in the genome by ZFN to date (FIG. 3) and we predict that we can use it to deliver even larger construct such as BACs into a pre-defined genomic locus, which is very challenging, if not impossible, to achieve via HR.

Beyond the practical value of our method, it can be used as a new tool in the study of NHEJ and the crosstalk between NHEJ and HR. Although similar strategies were reported using the I-SceI homing endonuclease (Certo et al., 2011), our strategy allows us to track any endogenous locus that can be targeted by ZFNs. We are interested in using this reporter system to monitor differential utilizations of NHEJ and HR in cells before and after oncogenic transformation. We are also continuing to identify chemical and genetic modulators that influence the cells to choose NHEJ or HR.

REFERENCES

1. Andersson B S, Collins V P, Kurzrock R, Larkin D W, Childs C, Ost A, Cork A, Trujillo J M, Freireich E J, and Siciliano M J. 1995. KBM-7, a human myeloid leukemia cell line with double Philadelphia chromosomes lacking normal c-ABL and BCR transcripts. *Leukemia* 9: 2100-2108.
2. Bibikova M, Beumer K, Trautman J K, and Carroll D. 2003. Enhancing gene targeting with designed zinc finger nucleases. *Science* 300: 764.
3. Brown K D, Rathi A, Kamath R, Beardsley D I, Zhan Q, and Mannino J L. 2003. The mismatch repair system is required for S-phase checkpoint activation. *Nature Genetics* 33: 80-84.
4. Carette J E, Guimaraes C P, Varadarajan M, Park A S, Wuethrich I, Kotecki M, Cochran B H, Spooner E, Ploegh H L, and Brummelkamp T R. 2009. Haploid genetic screens in human cells identify host factors used by pathogens. *Science* 326:1231-1235.
5. Certo M T, Ryu B Y, Annis J E, Garibov M, Jarjour J, and Rawlings D J. 2011. Tracking genome engineering outcome at individual DNA breakpoints. *Nature Methods* 8: 671-676.
6. Chen F, Pruett-Miller S M, Huang Y, Gjoka M, Duda K, Taunton J, Frodin M, and Davis G D. 2011. High-frequency genome editing using ssDNA oligonucleotides with zinc-finger nucleases. *Nature Methods* 8: 753-757.
7. Christian M, Cermak T, Doyle E L, Schmidt C, Zhang F, Hummel A, Bogdanove A. J., and Voytas D F. 2010. Targeting DNA double-strand breaks with TAL effector nucleases. *Genetics* 186: 757-761.
8. Cui X, Ji D, Fisher D A, Wu Y, Briner D M, and Weinstein E J. 2011. Targeted integration in rat and mouse embryos with zinc-finger nucleases. *Nature Biotechnology* 29: 64-67.

9. DeKelver R C, Choi V M, Moehle E A, Paschon D E, Hockemeyer D, Meijsing S. H., Sancak Y, Cui X, Steine E J, Miller J C, Tam P, Bartsevich V V, Meng X., Rupniewski I, Gopalan S M, Sun H C, Pitz K J, Rock J M, Zhang L, Davis G. D., Rebar E J, Cheeseman I M, Yamamoto K R, Sabatini D M, Jaenisch R, and Urnov F D. 2010. Functional genomics, proteomics, and regulatory DNA analysis in isogenic settings using zinc finger nuclease-driven transgenesis into a safe harbor locus in the human genome. *Genome Research* 20: 1133-1142.

10. Doyon Y, Vo T D, Mendel M C, Greenberg S G, Wang J, Xia D F, Miller J C, Gregory P D, and Holmes M C. 2011. Enhancing zinc-finger-nuclease activity with improved obligate heterodimeric architectures. *Nature Method* 8: 74-79.

11. Fung H and Weinstock D M. 2011. Repair at single targeted DNA double-strand breaks in pluripotent and differentiated human cells. *PloS one* 6: e20514.

12. Hockemeyer D, Soldner F, Beard C, Gao Q, Mitalipova M, DeKelver R C, Katibah G E, Amora R, Boydston E A, Zeitler B, Meng X, Miller J C, Zhang L, Rebar E J, Gregory P D, Urnov F D, and Jaenisch R. 2009 Efficient targeting of expressed and silent genes in human ESCs and iPSCs using zinc-finger nucleases. *Nature Biotechnology* 27: 851-857.

13. Hockemeyer D, Wang H, Kiani S, Lai C S, Gao Q, Cassady J P, Cost G J, Santiago Y, Miller J C, Zeitler B, Cherone J M, Meng X, Hinkley S. J., Rebar E J, Gregory P D, Urnov F D, and Jaenisch R. 2011 Genetic engineering of human pluripotent cells using TALE nucleases. *Nature Biotechnology* 29: 731-734.

14. Hollick J J, Golding B T, Hardcastle I R, Martin N, Richardson C, Smith G C M, and Griffin R J. 2003. 2,6-Disubstituted pyran-4-one and thiopyran-4-one inhibitors of DNA-dependent protein kinase (DNA-PK). *Bioorganic and Medicinal Chemistry Letters* 13: 3083-3086.

15. Kim H, Um E, Cho S R, Jung C, Kim H, and Kim J S. 2011. Surrogate reporters for enrichment of cells with nuclease-induced mutations. *Nature Methods* 8: 941-943.

16. Kim Y-G, Cha J, and Chandrasegaran S. 1996. Hybrid restriction enzymes: Zinc finger fusions to Fok I cleavage domain. *Proceedings of the National Academy of Sciences of the United States of America* 93: 1156-1160.

17. Li H, Haurigot V, Doyon Y, Li T, Wong S Y, Bhagwat A S, Malani N, Anguela X. M., Sharma R, Ivanciu L, Murphy S L, Finn J D, Khazi F R, Zhou S, Rebar E J, Bushman F D, Gregory P D, Holmes M C, and High K A. 2011. In vivo genome editing restores haemostasis in a mouse model of haemophilia. *Nature* 475: 217-221.

18. Liang F, Romanienko P J, Weaver D T, Jeggo P A, and Jasin M. 1996. Chromosomal double-strand break repair in Ku80-deficient cells. *Proceedings of the National Academy of Sciences of the United States of America* 93: 8929-8933.

19. Maresca M, Erler A, Fu J, Friedrich A, Zhang Y, and Stewart A F. 2010. Single-stranded heteroduplex intermediates in Red homologous recombination. *BMC molecular biology* 11.

20. Meyer M, De Angelis M H, Wurst W, and Kuhn R. 2010. Gene targeting by homologous recombination in mouse zygotes mediated by zinc-finger nucleases. *Proceedings of the National Academy of Sciences of the United States of America* 107: 15022-15026.

21. Miller J C, Holmes M C, Wang J, Guschin D Y, Lee Y-L, Rupniewski I, Waite A J, Wang N S, Kim K A, Gregory P D, and Pabo C O. 2007. An improved zinc-finger nuclease architecture for highly specific genome editing. *Nature Biotechnology* 25: 778-785.

22. Mittelman D, Moye C, Morton J, Sykoudis K, Lin Y, Carroll D, and Wilson J H. 2009. Zinc-finger directed double-strand breaks within CAG repeat tracts promote repeat instability in human cells. *Proceedings of the National Academy of Sciences of the United States of America* 106: 9607-9612.

23. Moehle E A, Rock J M, Lee Y L, Jouvenot Y, DeKelver R C, Gregory P D, and Holmes M C. 2007. Targeted gene addition into a specified location in the human genome using designed zinc finger nucleases. *Proceedings of the National Academy of Sciences of the United States of America* 104: 3055-3060.

24. Oberdoerffer P, Otipoby K L, Maruyama M, and Rajewsky K. 2003. Unidirectional Cre-mediated genetic inversion in mice using the mutant loxP pair lox66/lox71. *Nucleic Acids Research* 31: e140.

25. Orlando S J, Santiago Y, DeKelver R C, Freyvert Y, Boydston E A, Moehle E. A., Choi V M, Gopalan S M, Lou J F, Li J, Miller J C, Holmes M C, Urnov F D, and Cost G J. 2010. Zinc-finger nuclease-driven targeted integration into mammalian genomes using donors with limited chromosomal homology. *Nucleic Acids Research* 38: e152.

26. Petek L M, Russell D W, and Miller D G. 2010. Frequent endonuclease cleavage at off-target locations in vivo. *Molecular Therapy* 18: 983-986.

27. Poliseno L, Salmena L, Zhang J, Carver B, Haveman W J, and Pandolfi P P. 2010. A coding-independent function of gene and pseudogene mRNAs regulates tumour biology. *Nature* 465: 1033-1038.

28. Porteus M H and Baltimore D. 2003. Chimeric nucleases stimulate gene targeting in human cells. *Science* 300: 763.

29. Pruett-Miller S M, Connelly J P, Maeder M L, Joung J K, and Porteus M H. 2008. Comparison of zinc finger nucleases for use in gene targeting in mammalian cells. *Molecular Therapy: the Journal of the American Society of Gene Therapy* 16: 707-717.

30. Radecke S, Radecke F, Cathomen T, and Schwarz K. 2010. Zinc-finger nuclease-induced gene repair with oligodeoxynucleotides: Wanted and unwanted target locus modifications. *Molecular Therapy* 18: 743-753.

31. Ramalingam S, Kandavelou K, Rajenderan R, and Chandrasegaran S. 2011. Creating designed zinc-finger nucleases with minimal cytotoxicity. *Journal of Molecular Biology* 405: 630-641.

32. Reyon D, Tsai S Q, Khgayter C, Foden J A, Sander J D, and Joung J K. 2012. FLASH assembly of TALENs for high-throughput genome editing. *Nature Biotechnology* 30: 460-465.

33. Rouet P, Smih F, and Jasin M. 1994. Introduction of double-strand breaks into the genome of mouse cells by expression of a rare-cutting endonuclease. *Molecular and Cellular Biology* 14: 8096-8106.

34. Sarkaria J N, Busby E C, Tibbetts R S, Roos P, Taya Y, and Karnitz L M. 1999. Inhibition of ATM and ATR kinase activities by the radiosensitizing agent, caffeine. *Cancer Research* 59: 4375-4382.

35. Smith J, Bibikova M, Whitby F G, Reddy A R, Chandrasegaran S, and Carroll D. 2000. Requirements for double-strand cleavage by chimeric restriction enzymes with zinc finger DNA-recognition domains. *Nucleic Acids Research* 28: 3361-3369.

36. Szczepek M, Brondani V, Buchel J, Serrano L, Segal D J, and Cathomen T. 2007. Structure-based redesign of the dimerization interface reduces the toxicity of zinc-finger nucleases. *Nature Biotechnology* 25: 786-793.
37. Urnov F D, Rebar E J, Holmes M C, Zhang H S, and Gregory P D 2010. Genome editing with engineered zinc finger nucleases. *Nature Reviews Genetics* 11: 636-646.
38. Xu Z-L, Mizuguchi H, Ishii-Watabe A, Uchida E, Mayumi T, and Hayakawa T. 2001. Optimization of transcriptional regulatory elements for constructing plasmid vectors. *Gene* 272: 149-156.
39. Zeevi V, Tovkach A, and Tzfira T. 2008. Increasing cloning possibilities using artificial zinc finger nucleases. *Proceedings of the National Academy of Sciences of the United States of America* 105: 12785-12790.

EXAMPLES

Example 1

Precise End-Joining by ObLiGaRe

In order to directly ligate an exogenous DNA fragment into the genome, we initially introduced ZFN binding sites in a donor plasmid with the same orientation as in the genome. However we found this strategy often yielded unpredictable products presumably because the same ZFN binding sites were produced after ligation which could then be repetitively digested, a process that could stimulate end recessing before joining (Pruett-Miller et al., 2008). One essential requirement for ZFN-mediated site-specific digestion using obligated heterodimers is that a pair of ZFNs needs to form heterodimers through the modified FokI nuclease domain after binding to their targeted DNA sequences on the opposite strands. We thought that if we altered the orientation of the genomic ZFN recognition sequences in the donor plasmid we could lock the ligation product in a palindrome of identical half ZFN recognition site which would be no longer sensitive to the same obligated heterodimeric ZFN pairs. We used the well-characterized AAVS1 ZFN binding sites (located in the second intron of PPP1R12C)(Hockemeyer et al., 2009) to illustrate this design principle (FIG. 1a). Here we inverted the two half AAVS1 ZFN binding sites in the vector without changing the orientation of the linker region (FIG. 1a, ObLiGaRe donor). The AAVS1 ZFNs cut both the genome and the donor plasmid to produce complementary overhangs. After ligation, the newly formed junctions are resistant to further digestion by AAVS1 ZFNs.

Figures 1, 1B:
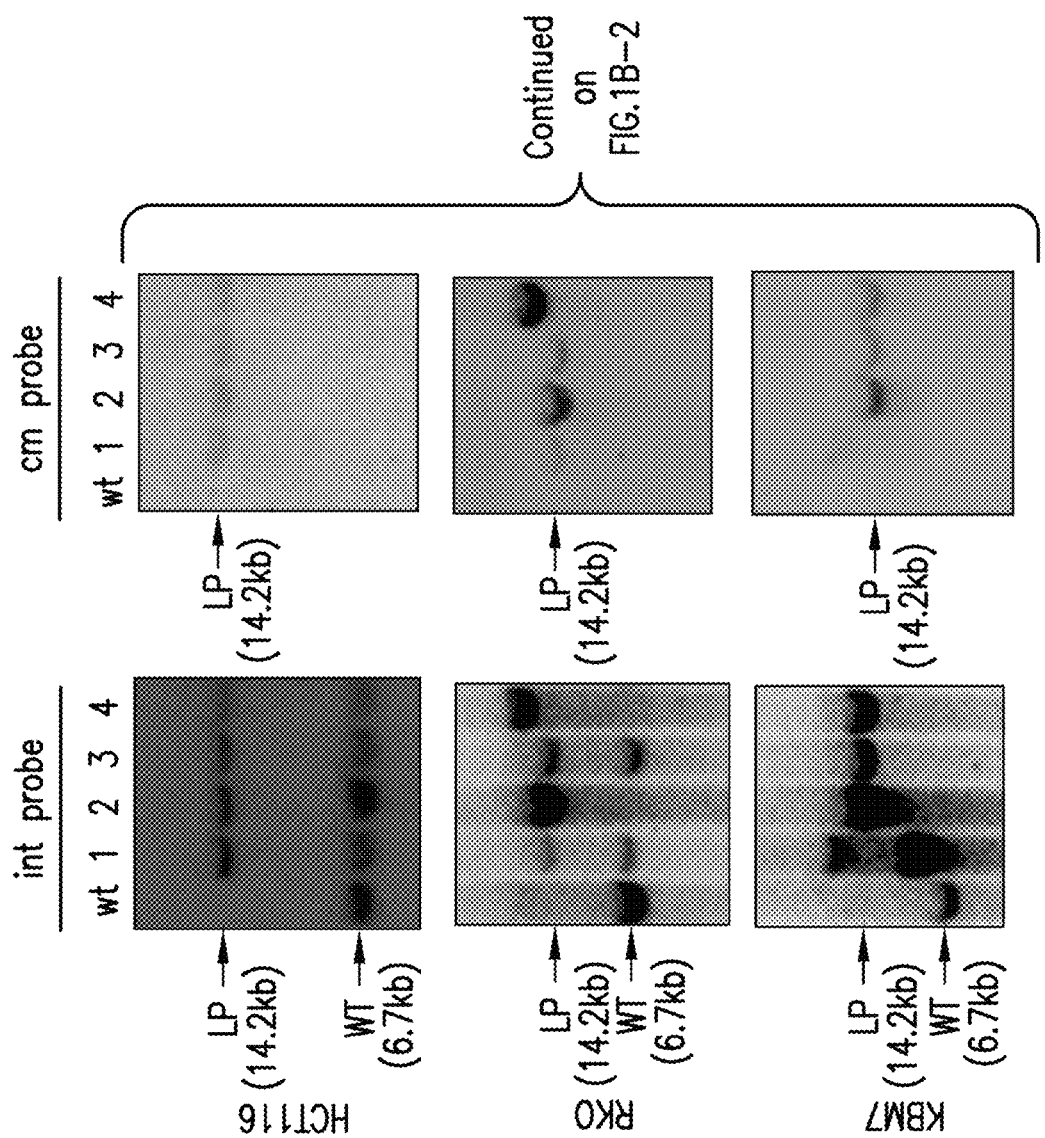

To test this hypothesis we constructed a vector containing the modified AAVS1 ZFN site followed by a promoterless T2A-puro cassette. Precise ligation of this cassette into the AAVS1 site in the genome would render the cells resistant to puromycin. We also included a constitutive GFP reporter driven by CAG promoter (Xu et al., 2001) in the vector to track the cells transfected with the plasmid. We transfected the donor plasmid into HCT116 cells either with or without the plasmids encoding AAVS1 ZFNs and observed an increase in the number of puromycin resistant colonies when the donor plasmid was co-transfected with the plasmids encoding AAVS1 ZFNs (data not shown). We randomly isolated four puromycin resistant, GFP positive clones and examined the vector integration by Southern blot. All four clones were heterozygous insertions of the vector as indicated with an AAVS1 locus specific probe (int probe, FIG. 1b). In addition, we did not observe random insertions of the vector in the genome when using a vector specific probe (CM probe, FIG. 1b). We then amplified the integration junctions by PCR and sequenced the PCR products. We found that 3 out of 4 clones had perfectly ligated junctions as predicted and one of them had a two nucleotides insertion in the linker region at the 5' junction (FIG. 1b). Similar results were obtained in RKO cells (FIG. 1b). Interestingly, one of the RKO clones turned out to be homozygous for a single copy vector insertion (clone #2). One clone (clone #4) was homozygous for a bigger insertion which might contain more than 1 copy of the vector.

We then tested ObLiGaRe in KBM7 cells. KBM7 is a close to haploid human myeloid leukemia cell line in which gene targeting has not been reported (Andersson et al., 1995; Carette et al., 2009). We co-transfected the donor plasmid with plasmids encoding AAVS1 ZFNs into KBM7 cells. Since the transfection efficiency was low we sorted GFP positive cells by FACS and subjected them for puromycin selection. We characterized 4 puromycin resistant clones and found 3 had correct insertions at the AAVS1 locus with no detectable random insertions as judged by Southern blot (FIG. 1b). Interestingly, the sequences of the junctions were very heterogeneous and often involved deletions probably between potential micro-homologies (FIG. 1b). It's important to add that the KBM7 resistant clones might have be originated from different cells as indicated by the appearance of additional bands and junctions sequences in the same clone (FIG. 1b).

Figure 2A:
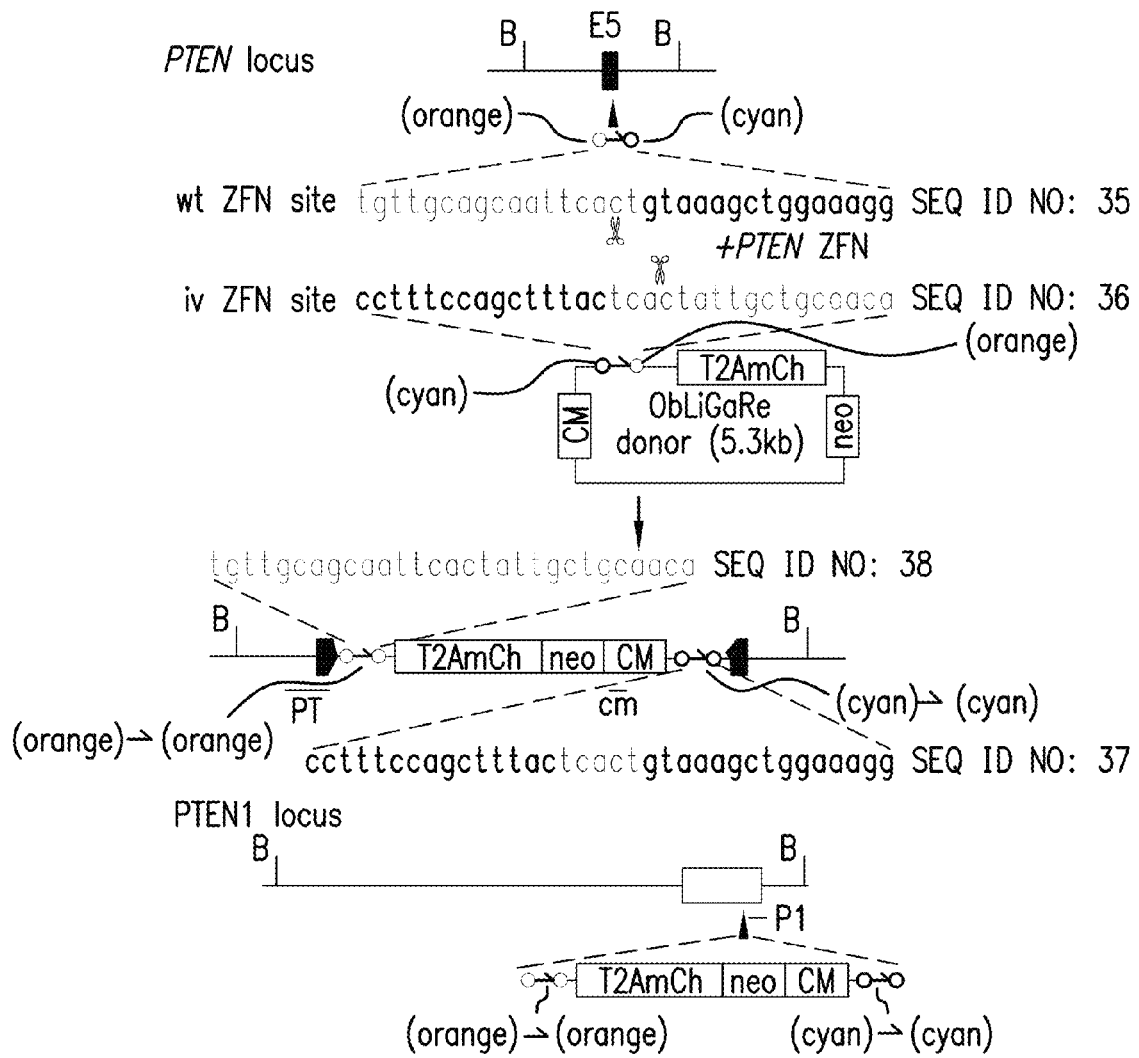
FIGS. 2A-2B ObLiGaRe at PTEN locus.
Figure 2B:
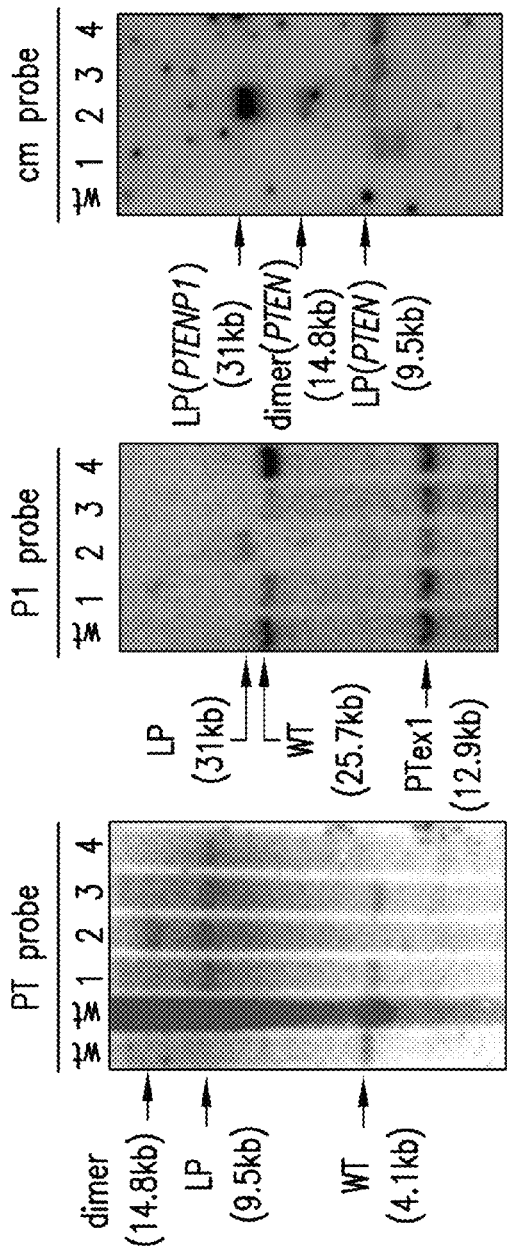

To determine whether ObLiGaRe is restricted to the AAVS1 locus and/or AAVS1 ZFNs, we used PTEN specific ZFNs to insert a vector containing a promoterless T2A-mCherry cassette and a CAG-neo selection marker into the PTEN locus in HCT116 cells. Human genome contains a PTEN pseudogene, PTENP1 (Poliseno et al., 2010) which is also targeted by the PTEN ZFNs. We isolated 4 G418 resistant clones and examined integration sites at both PTEN and PTENP1 loci by Southern blot. All clones had an insertion of the vector in PTEN locus, 2 are heterozygous (clones #1 & 3, FIG. 2b) for the insertion while 2 clones had an insertion on both alleles of PTEN (clones #2 & 3, FIG. 2b). Clone #2 had an insertion of one copy of the vector in one allele and a larger insertion in the other allele as indicated by the presence of a higher band (FIG. 2b). It also contained an insertion in PTENP1 locus (FIG. 2b). Interestingly, clones #1 had extra inserts in the genome as detected by the vector specific probe (CM probe) which might have been the result of either random insertion or insertion in other unidentified locus cleaved by PTEN ZFNs. However all the clones showed the precise predicted sequences at the junction between PTEN and T2A-cherry while clone #2 presents additional insertions at the junctions of the second targeted allele of both PTEN and PTENP1 (FIG. 2b table).

Figure 3A:
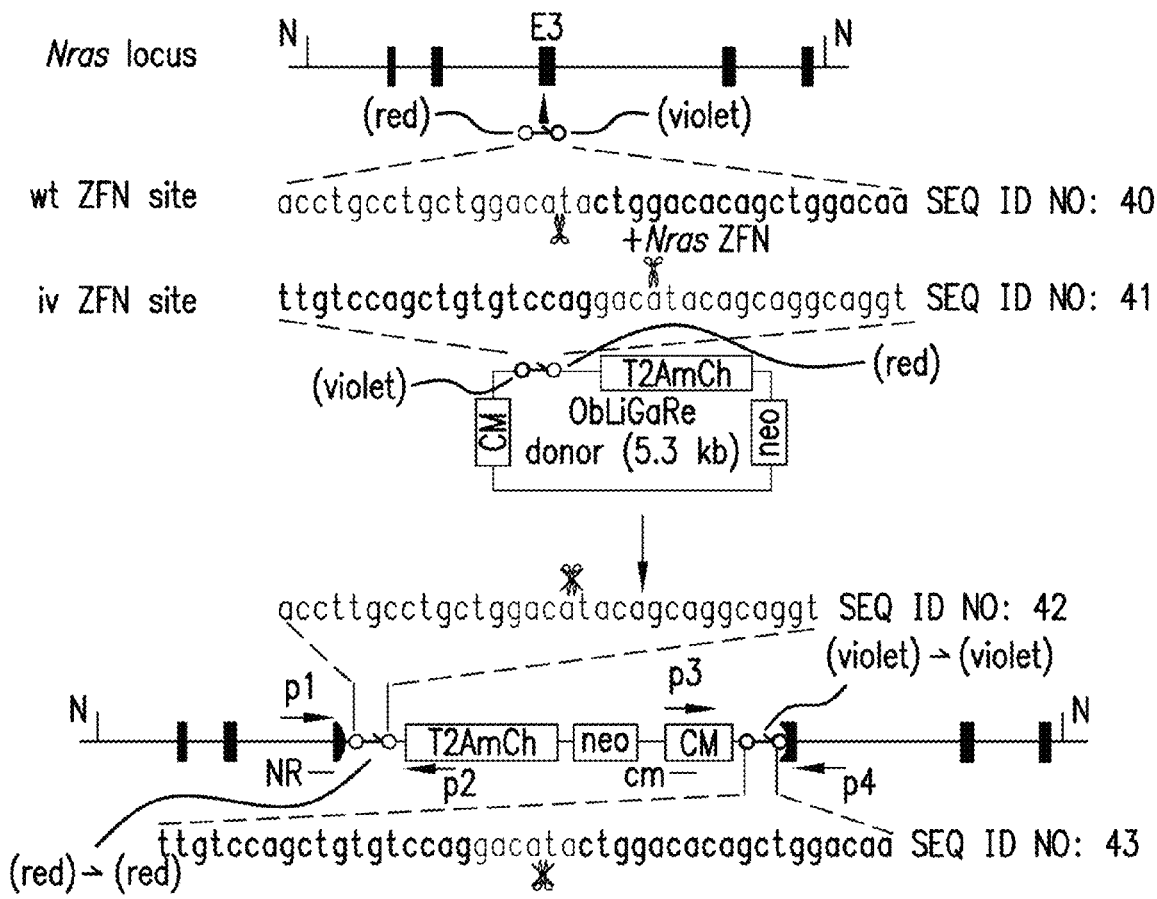
Figure 3B:
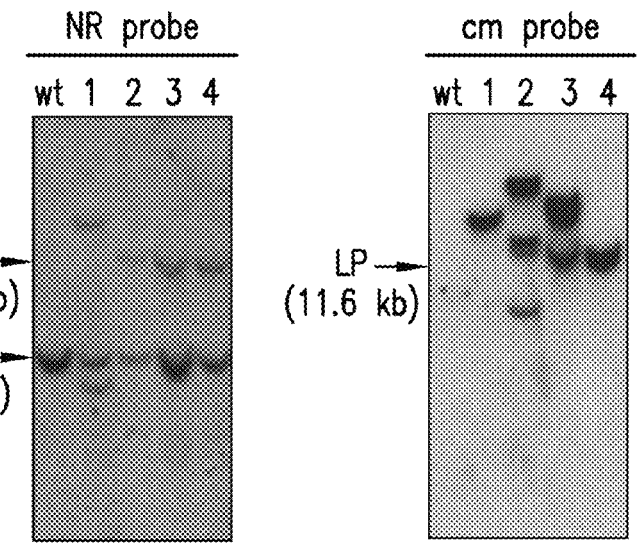

In order to test whether ObLiGaRe does not rely on any specific mutations in HCT116 and RKO cells which are known to be defective in DNA mismatch repairs (Brown et al., 2003), we decided to use a pair of ZFNs to target exon3 of Nras gene in mouse myoblast C2C12 cells (FIG. 3a). We co-transfected C2C12 cells with either Nras ZFNs alone or Nras ZFNs plus an ObLiGaRe vector containing a promoterless T2AmCherry cassette with a PGKneo selection marker and determined targeted integration in 4 randomly selected G418 resistant, mCherry fluorescent clones by Southern blot. All the clones showed targeted insertion of the vector at Nras locus as well as additional genomic insertion events except clone #4 (FIG. 3b). We sequenced the junctions between Nras and mCherry and confirmed that all 4 clones had precise end joining (data not shown). Finally, we applied the same strategy to target primary mouse embryonic fibroblast (MEF) cells. Since we could not perform clonal selection with MEFs, we pooled cells 3 days after transfection. We genotyped the pools by genomic PCR using primers that were specific for both 5' and 3' junction. We observed PCR products expected for correct integration only in cells transfected with ObLiGaRe vector and Nras ZFNs pair (FIG. 3c). We cloned the PCR products in a TOPO TA vector and sequenced 6 clones for each end. Majority of the sequences were the precise end joining sequence at both 5' and 3' ends (FIG. 3c).

Insertion of a 15 kb inducible gene expression cassette by ObLiGaRe at the AAVS1 locus.

Figure 4A:
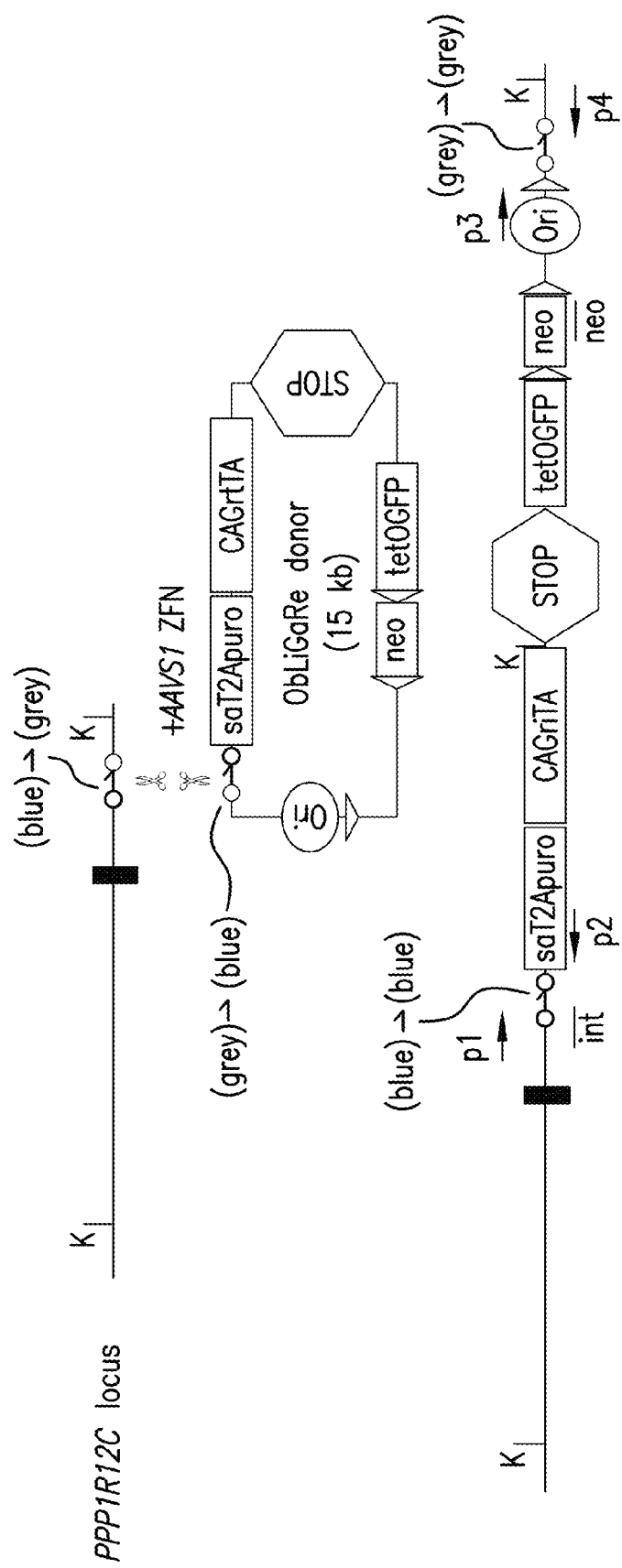
FIGS. 4A-4C Introduce a 15 kb inducible gene expression cassette in AAVS1 locus by single step ObLiGaRe.
Figure 4B:
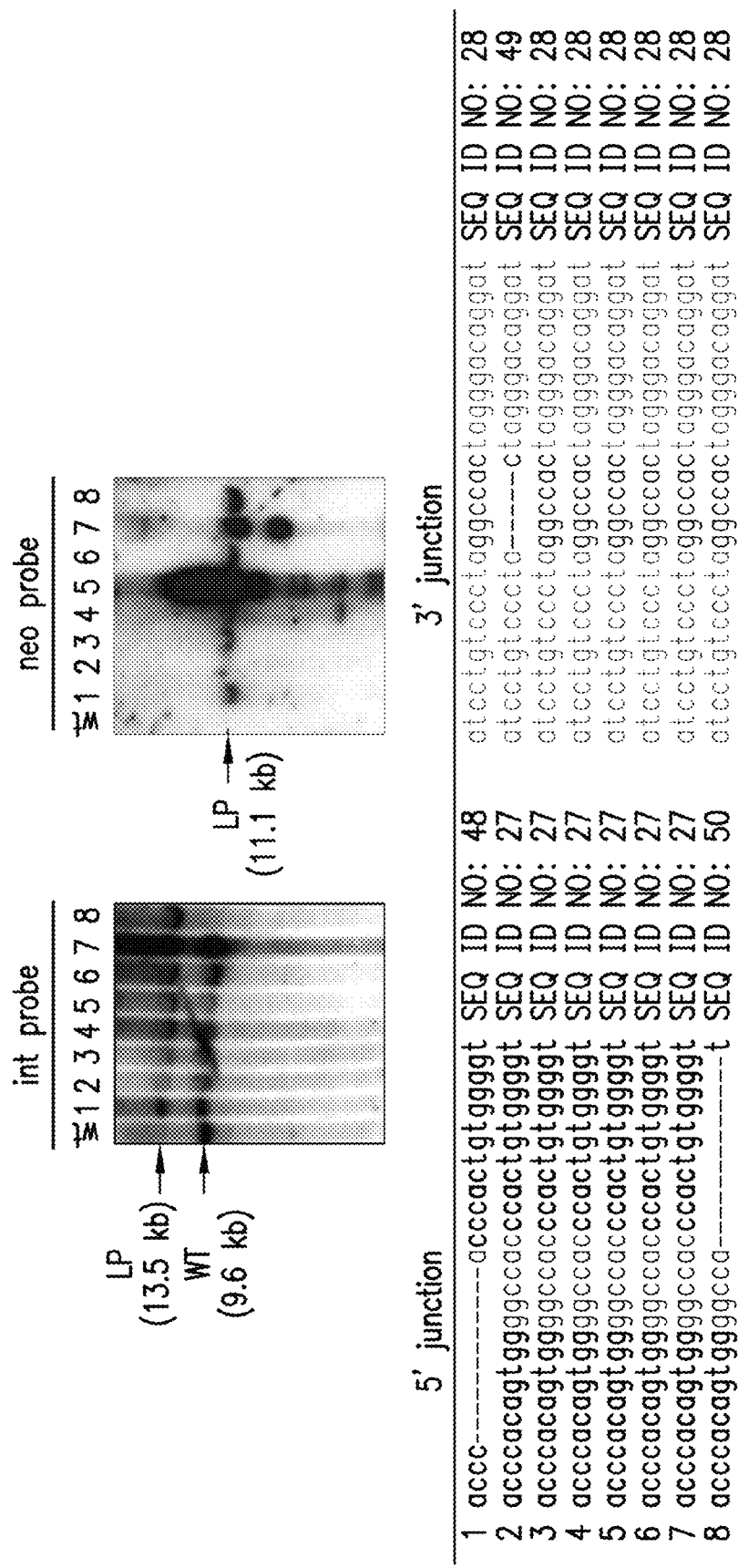
Figure 4C:
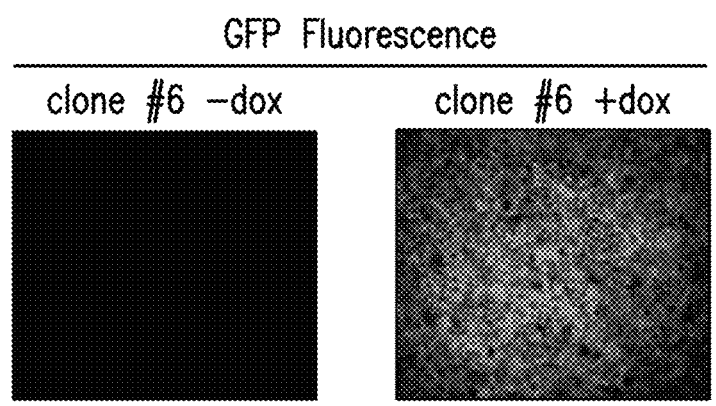

Previously inducible transgene expression from the AAVS1 locus was achieved by targeting a tetracycline controlled responder in the AAVS1 locus followed by delivery of the reverse tetracycline transcription activator (rtTA) by lentiviral transduction or by gene targeting in a second allele of AAVS1 (DeKelver et al., 2010; Hockemeyer et al., 2009). We decided to determine whether ObLiGaRe could facilitate insertion of the entire 15 kb transgenic cassette into the AAVS1 locus in a single step which has not been reported before. We inserted the modified AAVS1 ZFN site at the 5' of an inducible cassette that contains all the components for doxycycline-induced transgene expressions in mice (Yi Yang, unpublished data) and co-transfected it with AAVS1 ZFNs in HCT116 cells. We screened 18 puromycin resistant clones for correct integrations by PCR and identified 14 have expected PCR product (data not shown). We chose 8 positive clones for further analysis by Southern blot and showed all of them had correct integration (FIG. 4b). We observed precise end joining in the majority of 8 clones tested at both 5' and 3' junctions (FIG. 4b). Furthermore we could induce GFP expression by adding doxycycline in all 8 clones as shown with clone#6 (FIG. 4c).

Example 2

Mechanism of ObLiGaRe

Figure 5A:
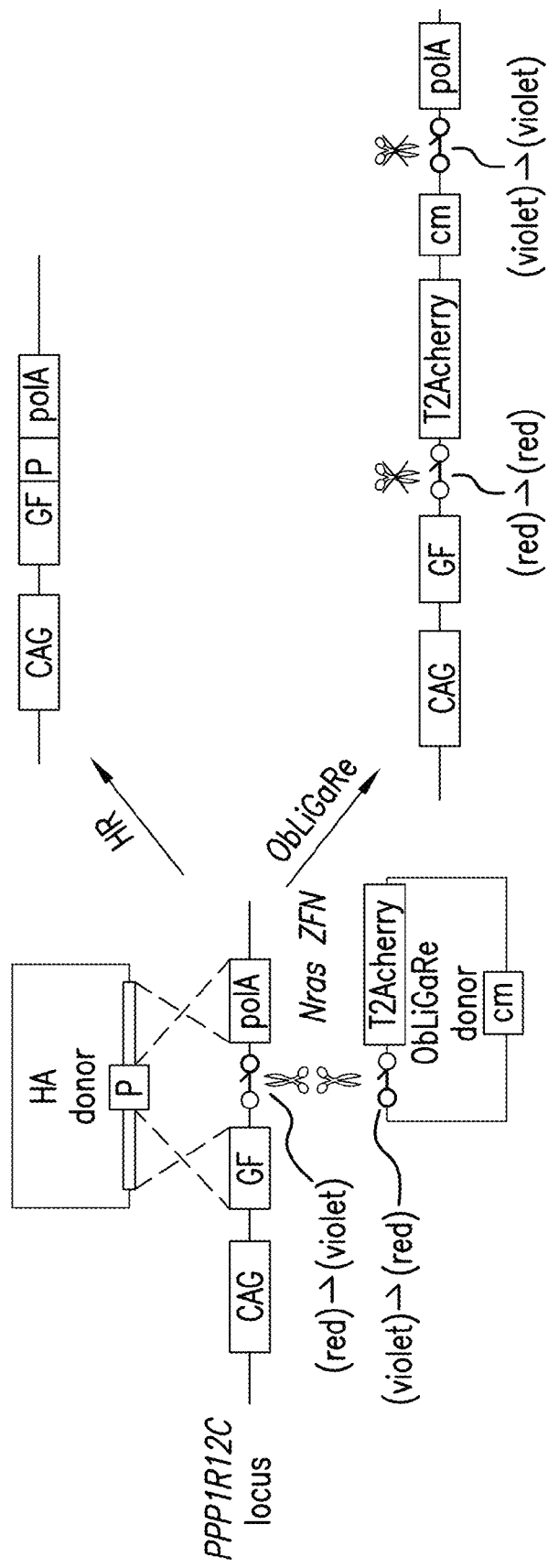
FIGS. 5A-5C ObLiGaRe is mediated via NHEJ.
Figure 5B:
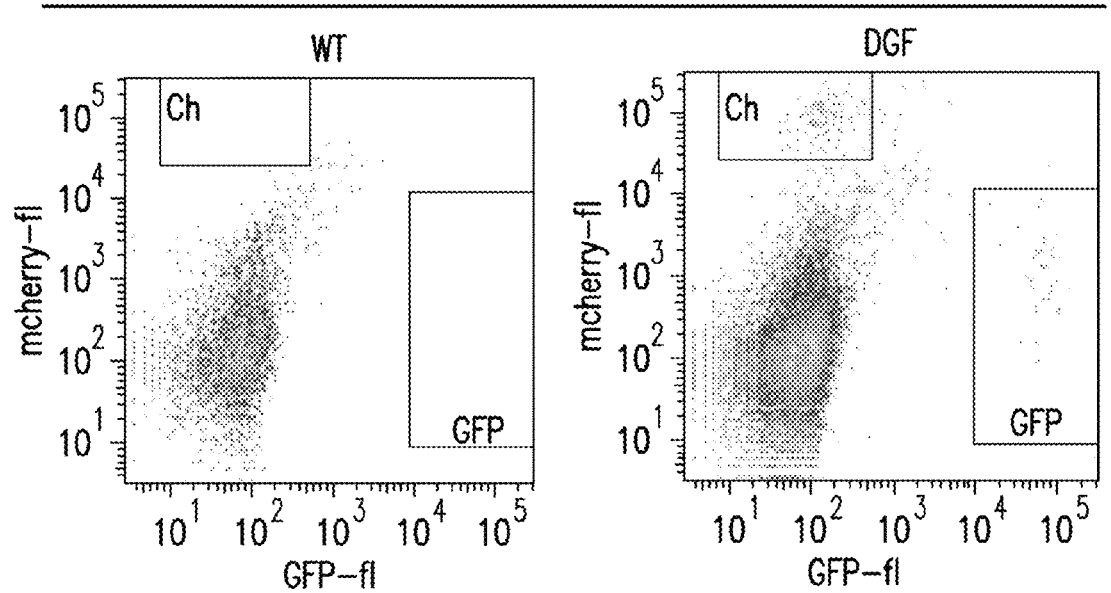
Figure 5C:
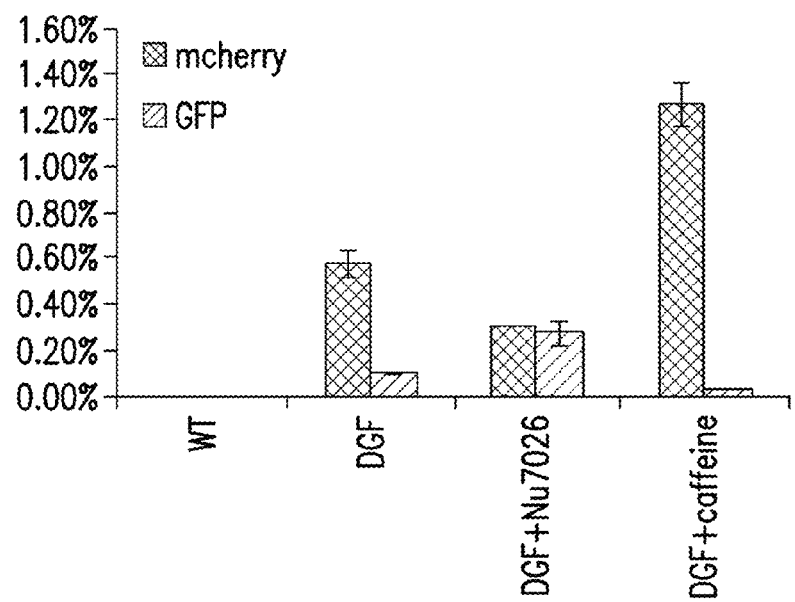

We speculated that ObLiGaRe might be mediated by NHEJ since it dose not require any homology between the donor and the target. To test this hypothesis, we inserted a defective GFP (DGF) harboring a mouse Nras ZFN recognition site at the AAVS1 locus by HR in HCT116 cells (FIG. 5a). We chose one of the correctly heterozygous targeted clones as a reporter (Clone#10 FIG. 7A-7C). We co-transfected Nras ZFNs with 2 plasmids to measure ObLiGaRe vs. HR simultaneously. One had 500 bp homology arms to the DGF and could reconstitute functional GFP by HR; the other had a modified Nras ZFNs site 5' to a promoterless T2A-mCherry cassette which would lead to mCherry expression upon insertion by ObLiGaRe (FIG. 5a). We FACS sorted cells and detected 6 times more mCherry positive cells than GFP positive cells in the reporter line but not the parental line (FIG. 5b). All clones derived from the mCherry fluorescent cells presented precise end joining of the mCherry with the defective GFP (data not shown). Interestingly, when we added 10 □M Nu7026 (Hollick et al., 2003) to the medium, a potent inhibitor of DNA-PK, the number of mCherry fluorescent cells was significantly reduced whereas that of GFP fluorescent cells was increased (p<0.001, FIG. 5c), suggesting ObLiGaRe requires DNA-PK, a key component of NHEJ. On the other hand the addition of 4 mM caffeine to the medium, a non specific inhibitor of the ATM and ATR kinases which are involved in HR pathway (Sarkaria et al., 1999), causes a significant increase of mCherry fluorescent cells with a decrease of GFP fluores-cent cells (p<0.001, FIG. 5c). We plan to use our reporter system to study the balance between homologous recombination and NHEJ.

Example 3

Cell Culture and Transfections

HCT116 and RKO (American Type Culture Collection, VA) were cultured in McCoy's 5A medium (Life Technologies, CA) supplemented with 10% fetal bovine serum (Life Technologies, CA). C2C12 (American Type Culture Collection, VA) were cultured in Dulbecco's modified Eagle's medium supplemented with 10% fetal bovine serum (Life Technologies, CA). KBM7 cells, were cultured in IMDM Glutamax (Life Technologies, CA) supplemented with 10% fetal bovine serum. HCT116, RKO, C2C12 and MEFs cells were plated in 6-wells plates (50-80% confluence) and transfected with Lipofectamine LTX according to manufacture's instructions. Briefly, 2 g of ZFNs plasmid and 0.5 g of ObLiGaRe vector were mixed with 12 l of Lipofectamine LTX reagent and co-transfected into $5 \times 10^5$ cells. 2 days after transfection cells were transferred to 15 cm plates and subject to either puromycin (Life Technologies, CA) selection (0.5 g/ml) or G418 (Life Technologies, CA) selection (100 g/ml) the following day. GFP positive, puromycin resistant clones were harvested after 15 days of selection. $10^7$ KBM7 cells were electroporated with 8 g of ZFN plasmids and 2 g of ObLiGaRe donor using Gene PulserII electroporation system (Bio-Rad, Melville, N.Y.) with electrical settings of 250 V and 950 µF. GFP positive cells were sorted by FACS (Y-Aria Becton Dickinson, NJ) two days after transfection and 100 GFP positives cells were seeded in 12 wells and selected with puromycin (1.0 g/mL); GFP positives, puromycin resistant clones (pools) were harvested after 10 days of selection.

Example 4

Comparing Homologous Recombination to ObLiGaRe $2 \times 10^5$ reporter cells were transfected with 0.2 g ZFN plasmid, 0.3 g ObLiGaRe donor (Ob) and 0.5 g HA donor plasmids (HA), using 4 L Lipofectamine LTX in 12 wells.

The percentage of GFP and mCherry positive cells was measured using FACS cantol flow cytometer (Becton Dickinson, NJ) 4 days after transfection.

Treatment with Nu7026 (Sigma Aldrich, MO) was started one day before transfection with a final concentration of 10 M Nu7026 (from a 10 mM stock solution in DMSO) and was continued for 2 days after transfection.

ANOVA and Tukey's HSD tests were adopted to perform statistical analysis using R statistics software.

ZFN Expression Plasmids

ZFNs against the human PTEN and Nras loci were designed and manufactured by Sigma-Aldrich. ZFNs and TALENs used in this work carried obligate heterodimer forms of the FokI endonuclease. AAVS1 ZFNs and TALENs were made according to (Hockemeyer et al., 2009; Hockemeyer et al., 2011). The ZFN expression constructs were obtained by Sigma-Aldrich but modified to insert both ZFNs in one plasmids using ad h.o.c. recombination (Maresca et al. unpublished).

PCR Primers:

| | | |
|---|---|---|
| Southern blot internal probe for AAVS1 | 5'-tttctgtctgcagcttgtgg (SEQ ID NO: 1) | 5'-gggtggaggggacagataaa (SEQ ID NO: 2) |
| AAVS1 5' ObLiGaRe | 5'-cccctatgtccacttcagga (SEQ ID NO. 3) | 5'-tgaggaagagttcttgcagct (SEQ ID NO: 4) |
| AAVS1 3' ObLiGaRe | 5'-tggctcattagggaatgctt (SEQ ID NO: 5) | 5'-acaggaggtggggttagac (SEQ ID NO: 6) |
| Southern blot probe for CM | 5'-tcactggatataccaccgttg (SEQ ID NO: 7) | 5'-tggtctgacagttattacgcc (SEQ ID NO: 8) |
| Southern blot probe for hPTEN | 5'-gctgcagtccattgagcata (SEQ ID NO: 9) | 5'-gctgtggtgggttatggtct (SEQ ID NO: 10) |
| Southern blot probe for hPTENP1 | 5'-attcgtcttctccccattcc (SEQ ID NO: 11) | 5'-agtgaattgctgcaacatga (SEQ ID NO: 12) |
| hPTEN 5' ObLiGaRe | 5'-aagaccataacccaccacagc (SEQ ID NO: 13) | 5'-ttggtcaccttcagcttggc (SEQ ID NO: 14) |
| hPTENP1 5' ObLiGaRe | 5'-aaagacattatgacaccgcc (SEQ ID NO: 15) | 5'-ttggtcaccttcagcttggc (SEQ ID NO: 16) |
| Southern blot probe for Nras | 5'-gttccagtgccctgttcaat (SEQ ID NO: 17) | 5'-cacaaccacttcccgaaact (SEQ ID NO: 18) |
| Nras 5' ObLiGaRe | 5'-ctgttagcgggttgagggta (SEQ ID NO: 19) | 5'-aagcgcatgaactccttgat (SEQ ID NO: 20) |
| Nras 3' ObLiGaRe | 5'-attaatgcagctggcacgac (SEQ ID NO: 21) | 5'-tggcaaatacacagaggaacc (SEQ ID NO: 22) |
| Southern blot probe for neo | 5'-gatcggccattgaacaagat (SEQ ID NO: 23) | 5'-gcgataccgtaaagcacgag (SEQ ID NO: 24) |

---

The invention claimed is:

1. A method of introducing a nucleic acid of interest into a locus of interest in a chromosome of a cell, said method comprising introducing into said cell:
   (1) a plasmid comprising:
      a) a zinc finger nuclease (ZFN) site comprising, in a 5' to 3' direction, a first half binding ZFN site, a spacer, a second half-ZFN binding site; and
      b) said nucleic acid of interest; and
   (2) a heterodimeric ZFN capable of cleaving said ZFN site; wherein:
   said locus of interest comprises a nucleic acid comprising, in a 5' to 3' direction, said second half ZFN binding site, said spacer, and said first half ZFN binding site, and said introduction of (1) and (2) results in insertion of said nucleic acid of interest into said chromosome of said cell, and wherein upon said insertion, a zinc finder nuclease site comprising said first half binding ZFN site and said second half binding ZFN site is not reconstituted.

* * * * *

SEQUENCE LISTING

<160> NUMBER OF SEQ ID NOS: 57

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tttctgtctg cagcttgtgg                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gggtggaggg gacagataaa                                              20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3

-continued cccctatgtc cacttcagga                                         20

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgaggaagag ttcttgcagc t                                       21

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tggctcatta gggaatgctt                                         20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
acaggaggtg ggggttagac                                         20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tcactggata taccaccgtt g                                       21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tggtctgaca gttattacgc c                                       21

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gctgcagtcc attgagcata                                         20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gctgtggtgg gttatggtct                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
attcgtcttc tccccattcc                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
agtgaattgc tgcaacatga                                              20

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aagaccataa cccaccacag c                                            21

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ttggtcacct tcagcttggc                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aaagacatta tgacaccgcc                                              20

```
<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ttggtcacct tcagcttggc                                                     20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gttccagtgc cctgttcaat                                                     20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cacaaccact tcccgaaact                                                     20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ctgttagcgg gttgagggta                                                     20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aagcgcatga actccttgat                                                     20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
attaatgcag ctggcacgac                                                     20
```

```
<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tggcaaatac acagaggaac c                                              21

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gatcggccat tgaacaagat                                                20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gcgataccgt aaagcacgag                                                20

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
accccacagt ggggccacta gggacaggat                                     30

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
atcctgtccc taggccaccc actgtggggt                                     30

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
accccacagt ggggccaccc actgtggggt                                     30

<210> SEQ ID NO 28
```

```
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
atcctgtccc taggccacta gggacaggat                                          30

<210> SEQ ID NO 29
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
accccacagt ggggcccaac ccactgtggg gt                                       32

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
atcctgtccc taggccacta gggat                                               25

<210> SEQ ID NO 31
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
accccacagt ggggt                                                          15

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
atcctgtccc tagggacagg at                                                  22

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
atcctgtcca ctagggacag gat                                                 23

<210> SEQ ID NO 34
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
atcctgtccc taggacagga t                                              21

<210> SEQ ID NO 35
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
tgttgcagca attcactgta aagctggaaa gg                                  32

<210> SEQ ID NO 36
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
cctttccagc tttactcact attgctgcaa ca                                  32

<210> SEQ ID NO 37
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
cctttccagc tttactcact gtaaagctgg aaagg                               35

<210> SEQ ID NO 38
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
tgttgcagca attcactatt gctgcaaca                                      29

<210> SEQ ID NO 39
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
tgttgcagca attcactact attgctgcaa ca                                  32

<210> SEQ ID NO 40
<211> LENGTH: 36
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 40
acctgcctgc tggacatact ggacacagct ggacaa                                 36

<210> SEQ ID NO 41
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ttgtccagct gtgtccagga catacagcag gcaggt                                 36

<210> SEQ ID NO 42
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
acctgcctgc tggacataca gcaggcaggt                                        30

<210> SEQ ID NO 43
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ttgtccagct gtgtccagga catactggac acagctggac aa                          42

<210> SEQ ID NO 44
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
acctgcctgc tggacagcag gcaggt                                            26

<210> SEQ ID NO 45
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ttgtccagct gtgtccagga catactggac acagctggac aag                         43

<210> SEQ ID NO 46
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 46
ttgactggac acagctggac aag                                            23

<210> SEQ ID NO 47
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
acctgcctgc tggacacata cagcaggcag gt                                  32

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
acccacccac tgtggggt                                                  18

<210> SEQ ID NO 49
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
atcctgtccc tactagggac aggat                                          25

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
accccacagt ggggccat                                                  18

<210> SEQ ID NO 51
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
``` ccccctccacc ccacagtggg gccactaggg acaggattgg tgacagaaa         49

<210> SEQ ID NO 52
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
tttctgtcac caatcctggg gccactaggg acactgtggg gtggaggggg         49

<210> SEQ ID NO 53
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53 ccccctccacc ccacagtggg gccactaggg acactgtggg gtggaggggg         49

<210> SEQ ID NO 54
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
tttctgtcac caatcctggg gccactaggg acaggattgg tgacagaaa          49

<210> SEQ ID NO 55
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55 ccccctccacc ccacagtggg gccctaggga cactgtgggg tggagggg          48

<210> SEQ ID NO 56
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56 ccccctccacc ccacagtggg gccagggaca ctgtggggtg gagggg            46

<210> SEQ ID NO 57
<211> LENGTH: 252
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (15)..(238)
<223> OTHER INFORMATION: a, c, t, g, unknown or other

```
<400> SEQUENCE: 57
tgttgcagca attcnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnct     240 attgctgcaa ca                                                          252
```